United States Patent
Griffin et al.

(10) Patent No.: US 9,364,311 B2
(45) Date of Patent: Jun. 14, 2016

(54) ENDOSCOPIC SYSTEM FOR WINDING AND INSERTING A MESH

(71) Applicant: Covidien LP, Mansfield, MA (US)

(72) Inventors: Jeremy Griffin, Hamden, CT (US); Jacqueline Jones, Hamden, CT (US); Timothy Sargeant, Guilford, CT (US); Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 85 days.

(21) Appl. No.: 14/445,109

(22) Filed: Jul. 29, 2014

(65) Prior Publication Data
US 2015/0164628 A1      Jun. 18, 2015

Related U.S. Application Data

(60) Provisional application No. 61/915,730, filed on Dec. 13, 2013.

(51) Int. Cl.
*A61B 17/08*      (2006.01)
*A61F 2/00*      (2006.01)

(52) U.S. Cl.
CPC ....... *A61F 2/0063* (2013.01); *A61F 2002/0072* (2013.01)

(58) Field of Classification Search
CPC ............ A61B 17/00234; A61F 2/0063; A61F 2002/0072; A61F 2002/9522; A61F 2/844; A61F 2/95

USPC ...................... 623/1.11; 606/1, 151
See application file for complete search history.

(56) References Cited

U.S. PATENT DOCUMENTS

| | | | |
|---|---|---|---|
| 5,957,939 A * | 9/1999 | Heaven et al. | 606/151 |
| 6,391,060 B1 | 5/2002 | Ory et al. | |
| 6,408,656 B1 | 6/2002 | Ory et al. | |
| 6,443,964 B1 | 9/2002 | Ory et al. | |
| 6,451,032 B1 | 9/2002 | Ory et al. | |
| 6,478,727 B2 | 11/2002 | Scetbon | |
| 6,596,002 B2 | 7/2003 | Therin et al. | |
| 6,695,855 B1 | 2/2004 | Gaston | |
| 6,971,252 B2 | 12/2005 | Therin et al. | |
| 7,021,086 B2 | 4/2006 | Ory et al. | |
| 7,867,222 B1 * | 1/2011 | Tilton et al. | 606/1 |
| 2007/0032805 A1 | 2/2007 | Therin et al. | |
| 2011/0034942 A1 * | 2/2011 | Levin et al. | 606/151 |

* cited by examiner

Primary Examiner — Katherine M Shi

(57) ABSTRACT

An endoscopic system for winding and inserting a mesh into an abdominal cavity of a patient is provided. The endoscopic system includes an introducer having an elongated shaft extending distally therefrom. The shaft includes a split portion that defines an opening therealong. The split portion is configured to support the mesh within the opening. A furler defining a lumen is engageable with the split portion of the shaft and configured to exert a radial force onto the mesh that is supported by the split portion. Rotation of one of the furler and introducer with respect to the other winds the mesh inside the furler to a diameter smaller than a diameter of the lumen of the furler.

11 Claims, 8 Drawing Sheets

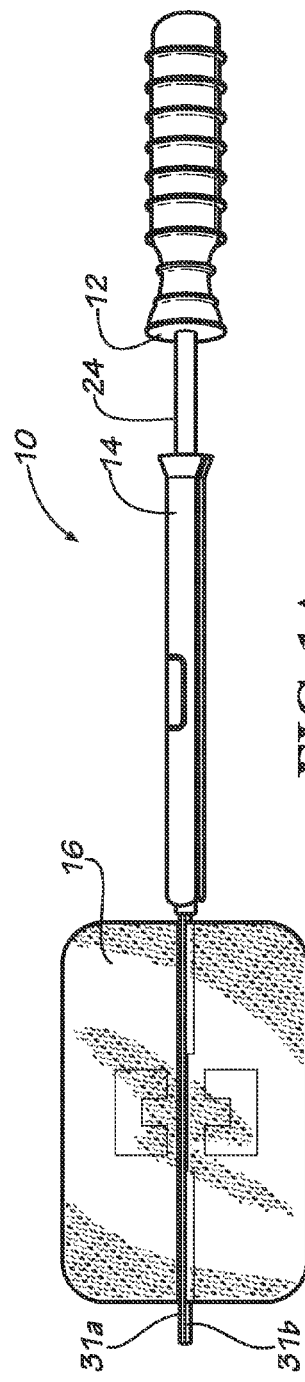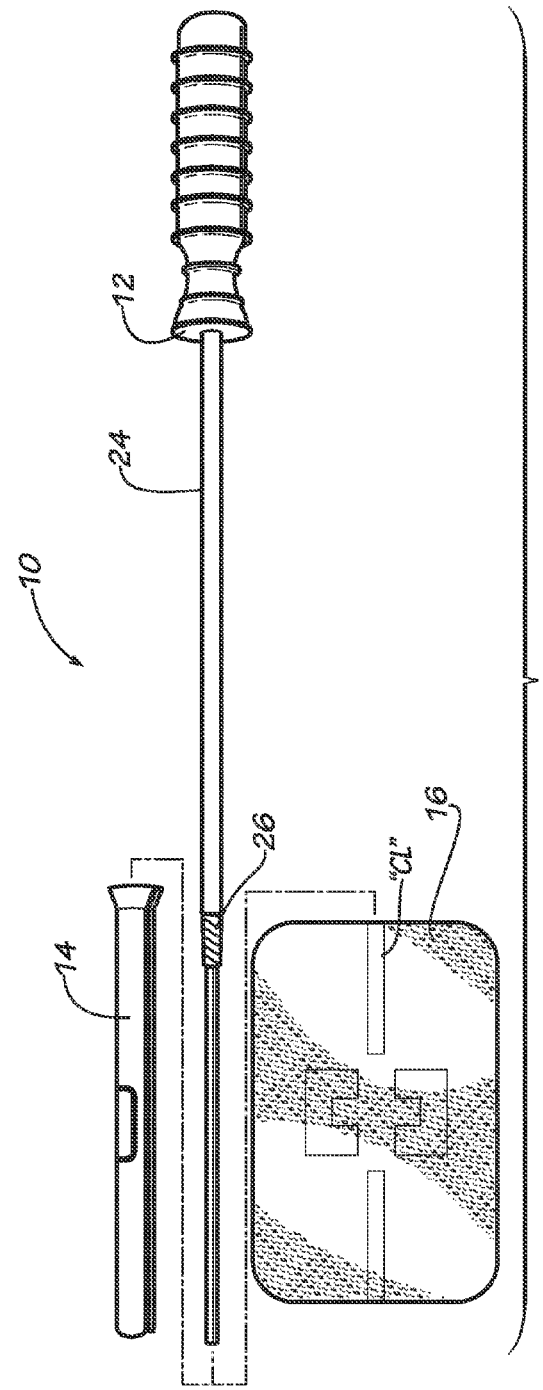

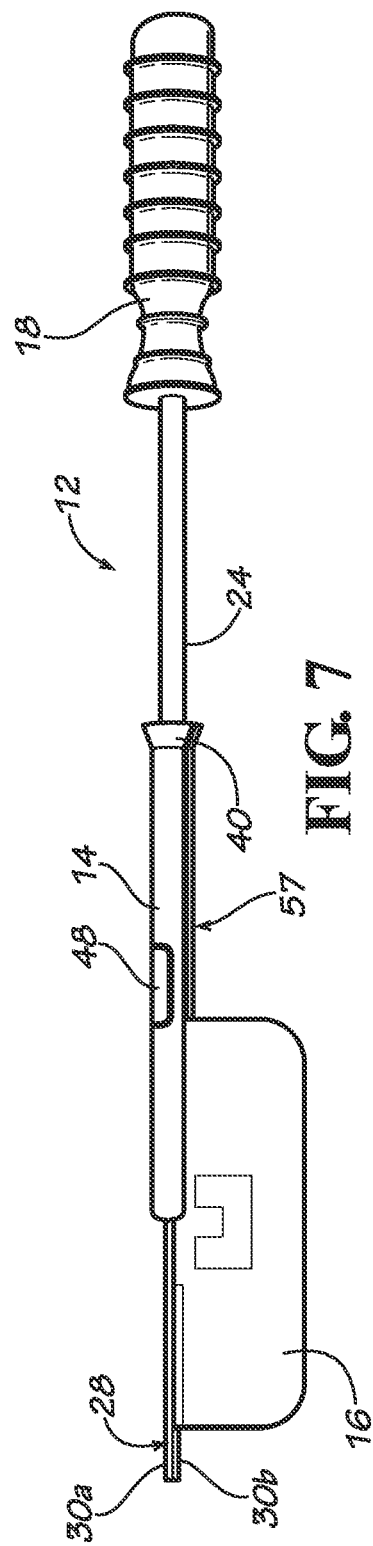
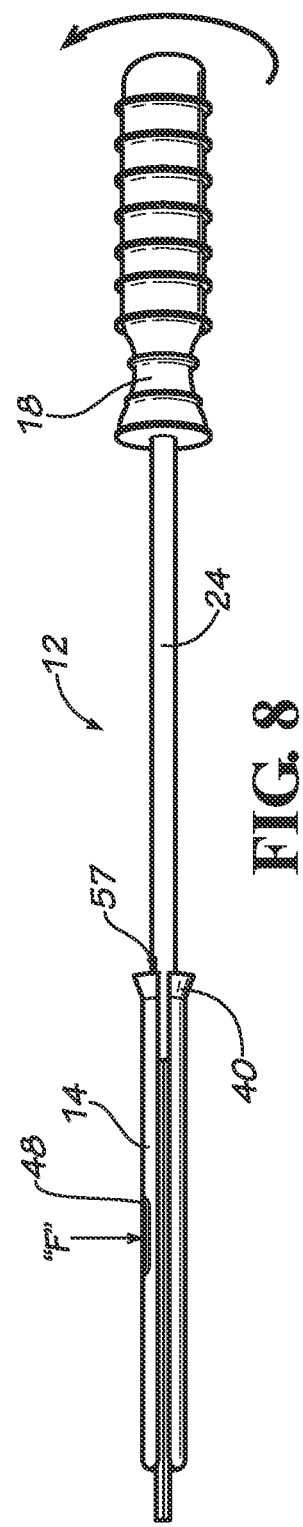

ENDOSCOPIC SYSTEM FOR WINDING AND INSERTING A MESH

CROSS-REFERENCE TO RELATED APPLICATIONS

This application claims the benefit of and priority to U.S. Provisional Patent Application No. 61/915,730, filed Dec. 13, 2013, the entire disclosure of which is incorporated by reference herein.

BACKGROUND

1. Technical Field

The present disclosure relates to an endoscopic system for winding and inserting mesh. More particularly, the present disclosure relates to an endoscopic system including an introducer and furler configured to wind and insert a mesh into an abdominal cavity of a patient.

2. Description of Related Art

Current mesh application typically requires a scrub nurse or other operating room personal to open, at the operating table, a pre-packaged sterile container containing a mesh, which may have a flat configuration. A surgeon will often remove the mesh from the opened container and mark the mesh with a marker and then roll or wind the mesh (e.g., like a scroll). The wound mesh is inserted into an abdominal cavity of a patient through an access port, e.g., a large diameter port (10 or 12 mm trocar) or through an open port site from which a trocar has been removed. In the latter case, after the mesh is inserted into the abdominal cavity, the trocar may be reinserted into the open port site to reenter the abdominal cavity. This additional step of reinserting the trocar adds time to the surgical procedure and can sometimes be difficult because of tissue plane movement.

While the aforementioned method for winding and inserting a mesh into an abdominal cavity of a patient may be satisfactory, a need exists for a simpler and less time-consuming method.

SUMMARY

As can be appreciated, an endoscopic instrument including an introducer and furler configured to wind (or roll) and insert a mesh into an abdominal cavity may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an endoscopic system for winding and inserting a mesh into an abdominal cavity of a patient. The endoscopic system includes an introducer having an elongated shaft extending distally therefrom. The shaft includes a split portion that defines an opening therealong. The opening of the split portion may extend to a distal tip of the shaft. The split portion is configured to support the mesh within the opening. A furler defining a lumen is engageable with the split portion of the shaft and configured to exert a radial force onto the mesh that is supported by the split portion. Rotation of one of the furler and introducer with respect to the other winds the mesh inside the furler to a diameter smaller than a diameter of the lumen of the furler.

The furler may be movable along the shaft to at least partially cover the mesh when the mesh is positioned within the split portion of the shaft. The furler may have an elongated configuration and a longitudinal slit extending along a length thereof. The longitudinal slit of the furler may be configured to receive the mesh when the mesh is supported on the split portion of the shaft.

The furler may include a tapered-down distal end defined by a v-shaped opening. The furler may include a flared proximal end having a conical configuration. The furler may include a medial portion having a tabbed cut-out defined by three side walls and a living hinge. The tabbed cut-out may be depressible to reduce the diameter of the lumen of the furler and apply the radial force to the mesh as the mesh is being wound.

The furler may include a pair of tension tabs extending radially from a center of the furler. Alternatively, the furler may include a pair of tension tabs extending tangentially from a center of the furler.

The shaft of the introducer may include an articulating portion positioned proximally in relation to the split portion. The endoscopic system may also include a sheath which is movable along the shaft and slidable within the furler.

Another aspect of the present disclosure provides a method that utilizes the endoscopic system for inserting a mesh into an abdominal cavity of a patient. The mesh is, initially, positioned through the split portion of the shaft. The furler, is then positioned over the split portion of the shaft to at least partially cover the mesh. Thereafter, one of the furler and shaft is rotated with respect to the other to wind the mesh inside the furler. A radial force is applied to the mesh, by reducing the diameter of the furler, as the mesh is being wound in the furler.

The furler including the wound mesh may then be inserted through an access opening in a patient. Further, the shaft may be pushed distally in relation to the access opening to engage a proximal end of the furler with the access opening to position the mesh into the abdominal cavity of a patient and unwind the mesh.

Positioning the mesh through the split portion of the shaft may further include positioning the mesh within the opening that extends along the split portion of the shaft. Moreover, prior to positioning the furler over the split portion of the shaft to at least partially cover the mesh, the mesh may be folded over the split portion of the shaft and at least a portion of the folded mesh may be positioned within the longitudinal slit of the furler. Rotating one of the furler and shaft with respect to the other to wind the mesh inside the furler may further include depressing the tabbed cut-out of the furler to apply the radial force to the mesh as the mesh is being wound, thereby facilitating a tight wind of the mesh and preventing unwinding of the mesh.

BRIEF DESCRIPTION OF THE DRAWING

Various embodiments of the present disclosure are described hereinbelow with references to the drawings, wherein:

FIG. 1A is a perspective view of an endoscopic system including an introducer, a furler and a mesh according to an embodiment of the instant disclosure;

FIG. 1B is a perspective view of the endoscopic system shown in FIG. 1A with parts separated;

FIGS. 7-11 are perspective views illustrating a method of use of the endoscopic system shown in FIG. 1A;

DETAILED DESCRIPTION

Figure 2:
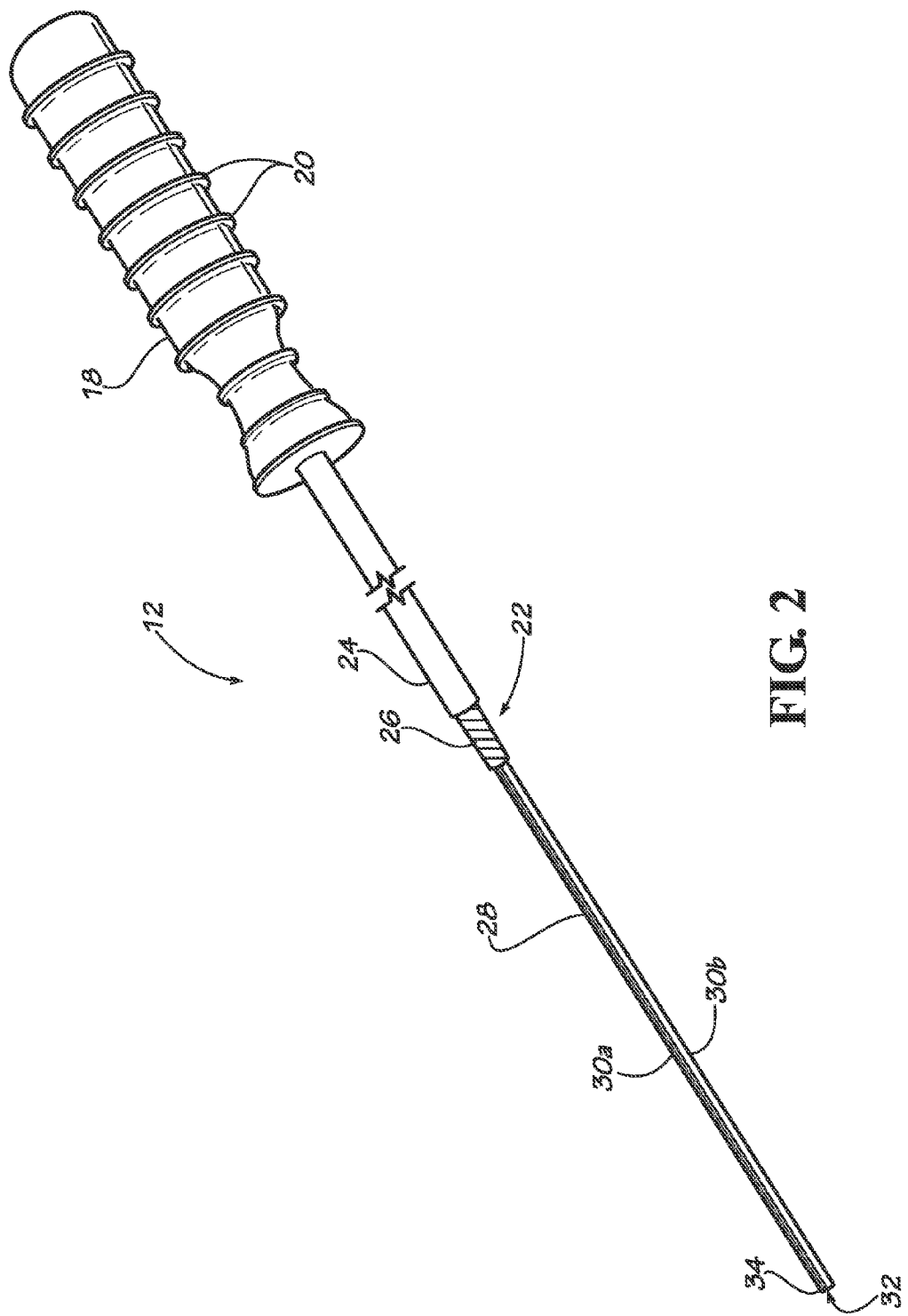
FIG. 2 is a perspective view of the introducer shown in FIGS. 1A and 1B.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As discussed above, an endoscopic system including an introducer and furler configured to wind (or roll) and insert a mesh into an abdominal cavity of a patient may prove useful in the surgical arena, and such an endoscopic system is described herein.

FIGS. 1A and 1B illustrate an endoscopic system 10 that includes an introducer 12 and a furler 14 which are configured to wind and insert one or more types of mesh 16 into an abdominal cavity of a patient. Suitable meshes include, but are not limited to, mesh that are formed via casting, molding, needle-punching, hooking, weaving, rolling, pressing, bundling, braiding, spinning, piling, knitting, felting, drawing, splicing, cabling, extruding, and/or combinations thereof. In some embodiments, the mesh 16 may further include reactive and/or may be bioabsorbable or non-bioabsorbable. The mesh 16 may have a thickness of from about 0.2 mm to about 5 mm, in embodiments, from about 1 mm to about 3 mm. Strands of the mesh 16 may be spaced apart to form pores of from about 100 microns to about 2000 microns in diameter, in embodiments, from about 200 microns to about 1500 microns, in other embodiments, from about 750 microns to about 1250 microns in diameter. Examples of various meshes include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

Filaments of the mesh 16 may be monofilament or multi-filament. Where multi-filament constructs are utilized, they may be plaited, braided, weaved, twisted, and the like, or laid parallel to form a unit for further construction into a fabric, textile, patch, mesh, and the like. The distribution of the filaments or strands may be random or oriented.

The mesh 16 may include natural or synthetic, bioabsorbable or non-bioabsorbable materials including those listed below. Suitable meshes include a collagen composite mesh such as PARIETEX™ (Tyco Healthcare Group LP, d/b/a Covidien, North Haven, Conn.) may be used. PARIETEX™ Composite mesh is a 3-dimensional polyester weave with a resorbable collagen film bonded on one side.

In embodiments, the mesh 16 component may be a substantially flat sheet (as described in the illustrated embodiments). In other embodiments, the mesh 16 may be cylindrical in shape.

In embodiments, the mesh 16 may act as a tissue scaffold, thereby providing a means for tissue integration/ingrowth. Such meshes are capable of providing cells with growth and development components. Thus, where a mesh is utilized as a tissue scaffold, it may assist in native tissue regrowth by providing the surrounding tissue with needed nutrients and bioactive agents. In some embodiments, as discussed herein, the mesh 16 itself may include a natural component, such as collagen, gelatin, hyaluronic acid, combinations thereof, and the like, and thus the natural component may be released or otherwise degrade at the site of implantation as the tissue scaffold degrades.

Continuing with reference to FIGS. 1A and 1B, the endoscopic system 10 may include or be utilized with one or more suitable access ports (e.g., trocar or radial sleeve with access openings ranging from about 5 mm to about 15 mm) to access the abdominal cavity of a patient to insert a wound mesh 16. Alternatively, the endoscopic system 10 can be utilized to insert the wound mesh 16 directly into the abdominal cavity through an incision in a patient.

FIG. 2 is a perspective view of the introducer 12. The introducer 12 includes a generally elongated configuration and has a handle 18, which may be ergonomically shaped to facilitate grasping and rotation of the introducer 12. In the illustrated embodiments, for example, a plurality of rib portions 20 are provided along a length of the handle 18 of the introducer 12 to facilitate grasping and rotation of the introducer 12.

Continuing with reference to FIG. 2, a shaft 22 extends from the handle 18 of the introducer 12. In the illustrated embodiments, the shaft 22 includes a first shaft portion 24 that extends distally from a distal end of the handle 18. The first shaft portion 24 connects to or supports an articulating or flexing portion 26 (shown schematically in FIG. 2) from which a second shaft portion 28 extends distally. The second shaft portion 28 pivotally connects to the articulating or flexing section 26 so that the second shaft portion 28 can be moved to one or more articulated or flexed configurations for positioning the mesh 16 within the abdominal cavity of a patient. In embodiments, the first and second shaft portions 24, 28 can be directly coupled to one another and the articulating or flexing portion 26 may be omitted.

The first shaft portion 24 has a generally elongated, cylindrical configuration and is configured to support the furler 14. The first shaft portion 24 has an outer diameter that allows the furler 14 to be moved along the first shaft portion 24 and over the mesh 16, which mesh 16 will be secured to or hung on the second shaft portion 28 and in a folded configuration, described in detail below. During insertion of the second shaft portion 28 into an access opening to insert the wound mesh 16 into the abdominal cavity, due to the size of the outer diameter of the first shaft portion 24, the furler 14 is able to move along the first shaft portion 24 to release the mesh 16 from the second shaft portion 28, also described in detail below.

The second shaft portion 28 may take the form of a splined shaft including two tines 30a, 30b that extend along a length of the second shaft portion 28. The two tines 30a, 30b are spaced-apart from one another and define a longitudinal opening 32 therebetween to form a fork or split configuration. The longitudinal opening 32 extends to a distal tip 34 that is configured to receive the mesh 16 so that the mesh 16 can be temporarily secured between the two tines 30a, 30b of the introducer 12.

In one method of use, once the mesh 16 is inserted between the two tines 30a, 30b of the introducer 12, the mesh 16 can be folded over the two tines 30a, 30b and the furler 14 can be positioned along the two tines 30a, 30b to cover the mesh 16, which can then be wound within the furler 14. Thereafter, the wound mesh 16 can be inserted into the abdominal cavity of a patient where the mesh 16 can be positioned adjacent target tissue with the articulating section 26 and/or released from between the tines 30a, 30b through the opening 32.

The introducer 12 including the handle 18 and first and second shaft portions 24, 28 may be formed from any suitable material, e.g., plastic, metal, ceramic, etc. For example, in embodiments, the handle 18 and first shaft portion 24 may be formed from a relatively rigid plastic and the tines 30a, 30b of the second shaft portion 28 may be formed from surgical steel. If the articulating portion 26 is provided with the introducer 12, the articulating portion 26 can be formed from plastic and/or surgical steel.

Turning now to FIGS. 3A and 4-6, the furler 14 is illustrated and will be described. The furler 14 can be formed from the same materials used to form the introducer 12. In the illustrated embodiments, the furler 14 may be formed from a relatively rigid plastic or stainless steel.

The furler 14 has a generally tubular configuration including proximal and distal ends 36, 38, respectively, and a medial portion 46 extending therebetween. Extending along the medial portion 46 of the furler 14 from the proximal end 36 to the distal end 38 is a longitudinal slot 37. The longitudinal slot 37 is configured to receive the mesh 16 when the mesh 16 is folded over the tines 30a, 30b so that the mesh 16 can be inserted into the furler 14 and wound.

Figure 4:
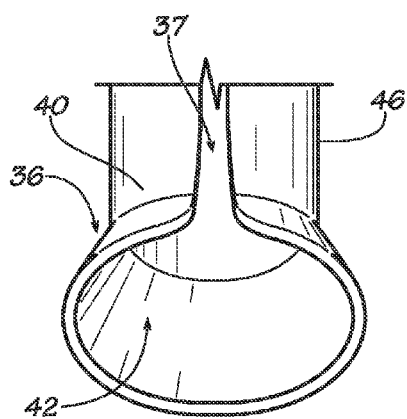
FIG. 4 is an indicated area of detail shown in FIG. 3A.

Referring to FIG. 4, the proximal end 36 includes a flared neck portion 40 that tapers outwardly to define an opening or lumen 42, which extends through the furler 14. The flared neck portion 40 has a conical configuration and includes a diameter that is greater than a diameter of the medial portion 46 and the distal end 38. The diameter of the flared neck portion 40 is also greater than a diameter of a proximal end of the access opening. This difference in diameter causes interference between the proximal end of the access opening and the flared neck portion 40 of the furler 14, which prevents the furler 14 from passing through the access opening as the second shaft portion 28 is being pushed distally therethrough to insert the wound mesh 16 into the abdominal cavity. Accordingly, the force that a user is applying to the introducer 12 after the flared neck portion 40 engages the proximal end of the access opening overcomes the frictional force between the wound mesh 16 and the furler 14 causing the wound mesh 16 to exit the furler 14 into the abdominal cavity of the patient. Additionally, the flared neck portion 40 provides a guide or funnel-like structure to facilitate alignment and insertion of the distal tip 34 of the second shaft portion 28 into the furler 14.

Figure 5:
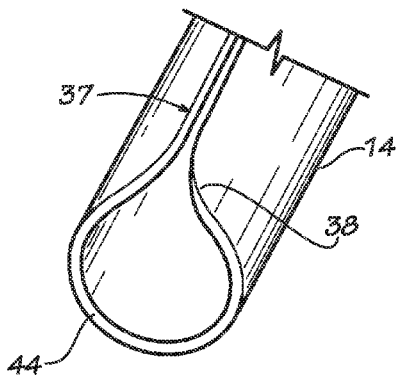
FIG. 5 is an indicated area of detail shown in FIG. 3A.

Referring to FIG. 5, the distal end 38 of the furler 14 includes a tapered down configuration having a generally v-shaped opening 44, which facilitates sliding the distal end 38 over the mesh 16 when the mesh 16 is folded over the tines 30a, 30b of the second shaft portion 28. The tapered down distal end 38 of the furler 14 also facilitates inserting the distal end 38 of the furler 14 into the access opening. The distal end 38 of the furler 14 may include other configurations not disclosed herein.

Figure 6:
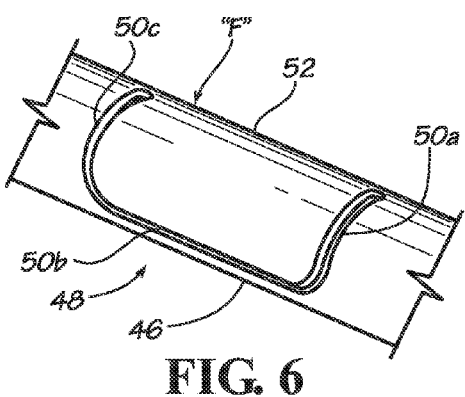
FIG. 6 is an indicated area of detail shown in FIG. 3A.

Referring to FIG. 6, the medial portion 46 of the furler 14 includes a tabbed cut-out 48 defined by three side walls 50a-50c and a living hinge 52, which allows the tabbed cut-out 48 to be depressed by a user to apply a radial force "F" normal or perpendicular (FIGS. 6 and 8) to the mesh 16 as the mesh 16 is being wound.

More particularly, in one embodiment of use, the tabbed cut-out 48 can be depressed and held by the user to effectively decrease the inside diameter of the furler 14 (i.e., to decrease a diameter of the lumen 42) to a point where the tabbed cut-out 48 comes into contact with the mesh 16. As the mesh 16 is being wound, and increasing in diameter within the furler 14, the tabbed cut-out 48 follows an outside diameter of the mesh 16 such that the application of the radial force "F" to the mesh 16 provides a tight wind of the mesh 16 (and prevents unwinding of the mesh 16). The tightly wound mesh 16 can be inserted into the abdominal cavity of the patient through a relatively smaller access opening, e.g., trocar with 5 mm opening, as compared to a wound mesh 16 that has not been more tightly wound due to the use of tabbed cut-out 48.

Figure 3A:
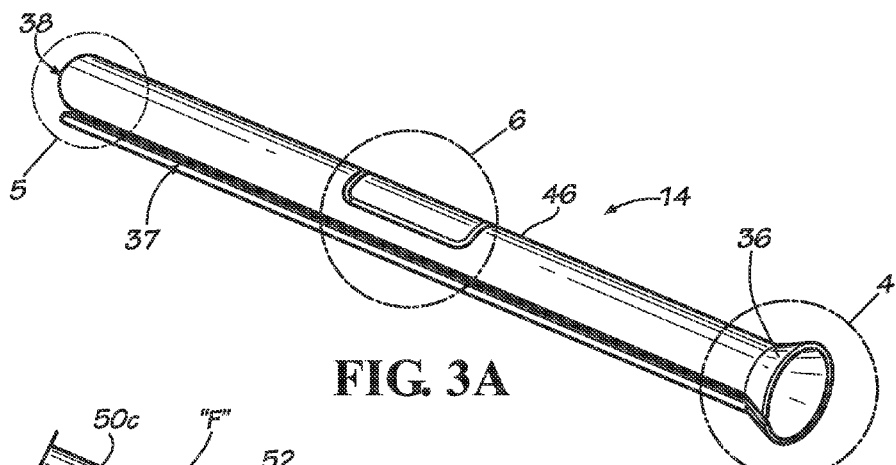
FIG. 3A is a perspective view of the furler shown in FIGS. 1A and 1B.
Figure 3B:
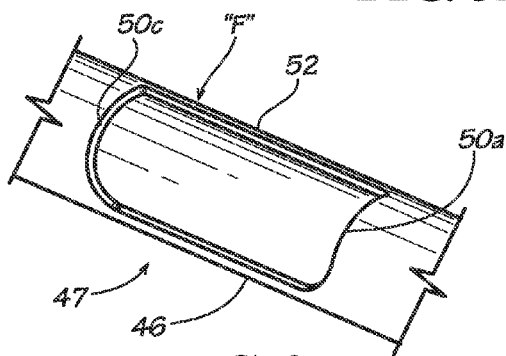
FIG. 3B is a partial, perspective view of a furler according to an alternate embodiment of the instant disclosure.

In embodiments, the tabbed cut-out 48 can be omitted and the furler 14 can be provided with a window 47 (FIG. 3B). In one embodiment of use, a user can position their thumb (or one of their fingers) within the window 47 to apply a radial force "F" normal or perpendicular to the mesh 16 as the mesh 16 is being wound to effectively decrease the inside diameter of the furler 14 (i.e., to decrease a diameter of the lumen 42) to a point where the user's thumb comes into contact with the mesh 16. As the mesh 16 is being wound, and increasing in diameter within the furler 14, the user's thumb follows an outside diameter of the mesh 16 such that the application of the radial force "F" to the mesh 16 provides a tight wind of the mesh 16 (and prevents unwinding of the mesh 16). The tightly wound mesh 16 can be inserted as described above.

Referring to FIGS. 7-11, a method of use of the endoscopic system 10 is now described. The components of the endoscopic system 10 may be packaged and shipped (in a sterile environment) separately, or together as a kit. In the latter instance, for example, the kit may include one or more of the aforementioned radial sleeves or trocar, the introducer 12, the furler 14 and the mesh 16. Conversely, the kit may be sold without the radial sleeves or trocar.

According to one embodiment of use, the furler 14 is, initially, positioned on the first shaft portion 24 towards the handle 18, with the tines 30a, 30b exposed (see FIG. 1A for example) or extending distally of the furler 14. The mesh 16 may be placed flat between the tines 30a, 30b, with the tines 30a, 30b in the center of the mesh 16. It is noted, the mesh 16 can be provided with a center-line "CL" to facilitate positioning the mesh 16 between the tines 30a, 30b (see FIG. 1B for example). The mesh 16 is then folded in half along the tines 30a, 30b (FIG. 7). In embodiments, such as when the endoscopic system 10 is sold as a kit, the mesh 16 can be pre-positioned between the tines 30a, 30b of the second shaft portion 28 and pre-wound within the furler 14.

The furler 14 is then slid distally along the first and second shaft portions 24, 28 with the longitudinal slot 57 of the furler 14 aligning with the folded mesh 16 so that the furler 14 covers the tines 30a, 30b with the two halves of the mesh 16 hanging out of the longitudinal slot 57 thereof (FIG. 7). It is noted that the furler 14 may be positioned completely or partially over the mesh 16 to wind the mesh 16.

Figure 9:
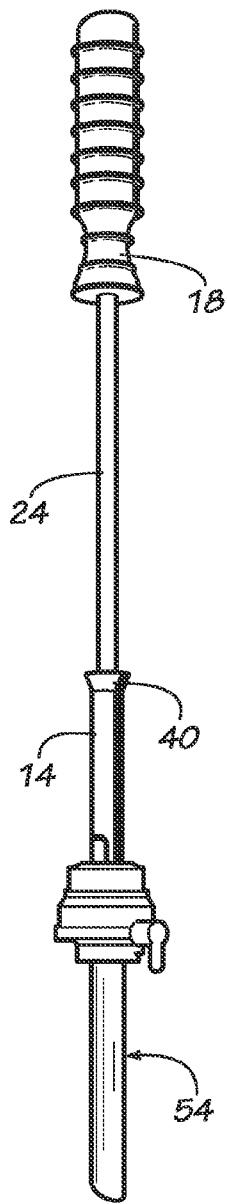

In one hand a surgeon holds the furler 14, and with the other hand rotates the handle 18 of the introducer 12, thereby rolling or winding the mesh 16 within the furler 14 (FIG. 8). Alternatively, the handle 18 of the introducer 12 can be held while the furler 14 is rotated with respect to the handle 12. In either instance, the tabbed cut-out 48 can be depressed as the mesh 16 is being wound in the furler 14 to provide a tight wind of the mesh 16. Desirably, the introducer 12 is rotated in a direction toward the sidewall 50b of the tabbed cut-out 48 (see FIG. 6) of the furler 14. Once the mesh 16 is fully wound, the introducer 12 including the furler 14 with the wound mesh 16 is inserted into a trocar 54 (FIG. 9).

Figure 10:
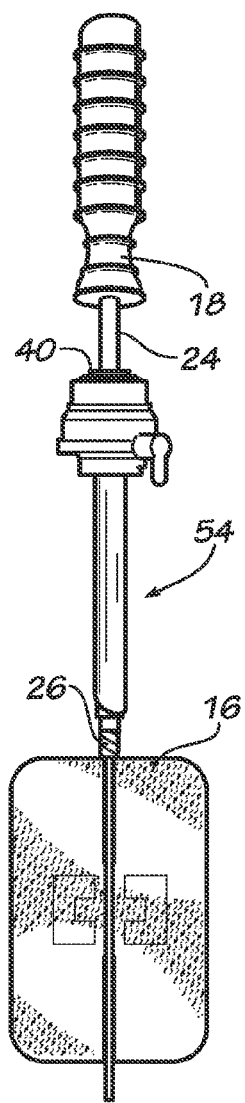
Figure 11:
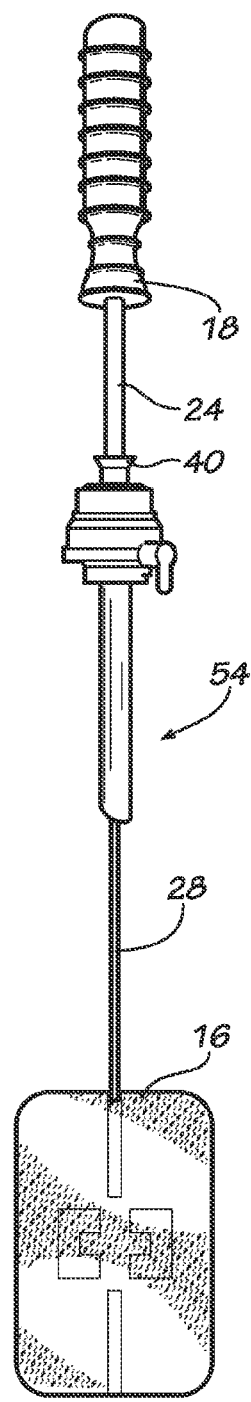

The furler 14 acts as a sheath which protects the mesh 16 as the mesh 16 is being inserted through the trocar 54. As the introducer 12 is being inserted into the trocar 54, the flared neck 40 on the proximal end 36 of the furler 14 contacts the proximal end of the trocar 54 preventing the furler 14 from going past a proximal end of the trocar 54 and completely entering the trocar 54 (FIG. 10). As the surgeon continues to insert the introducer 12 via the handle 18, the tines 30a, 30b advance the mesh 16 past the furler 14/trocar 54 and into the abdominal cavity of the patient, where the mesh 16 naturally unwinds (FIG. 10). At this point the surgeon can use the introducer 12 to roughly position (e.g., via the articulating portion 26 of the introducer 12) the mesh 16 for initial tacking, or simply remove the introducer 12, thereby allowing the mesh 16 to gently drop into the abdominal cavity (FIG. 11).

In accordance with the instant disclosure, the endoscopic system 10 allows for tight winding of the mesh 16 so that the mesh 16 can be inserted through trocars or radial sleeves that include relatively small access openings (e.g., 5 mm). As can be appreciated, this allows the surgeon to use smaller access ports, which, in turn, may prevent port site herniation and post-operative pain typically associated with larger port sites. Additionally, the furler 14 protects the mesh 16 from prematurely coming in contact with skin or underlying tissue.

From the foregoing and with reference to the various figure drawings, those skilled in the art will appreciate that certain modifications can also be made to the present disclosure without departing from the scope of the same. For example, the flared neck portion 40 of the furler 14 is one of many ways to create a stop that prevents the furler 14 from completely entering the access opening. For example, any number of tube forming operations could be utilized to achieve the same function. In embodiments, a flange (not shown) can be provided along an exterior surface of the furler 14 or a tab that extends radially outward from the furler 14 can also be used to create a stop that prevents the furler 14 from completely entering and/or exiting the access opening.

In embodiments, the introducer 12 may be provided with a pin or other suitable device (not explicitly shown) that aligns with the longitudinal slot 37 on the furler 14 to engage the longitudinal slot 37, thereby preventing the furler 14 from coming off of the introducer 12 upon removal from the access opening.

In embodiments, the handle 18 of the introducer 12 can have a trigger or button (not explicitly shown) for automatic deployment/unwrapping of the mesh 16, or can be powered to dispense/unravel/unwind the mesh 16 intra-abdominally with the push of the button.

Figure 12:
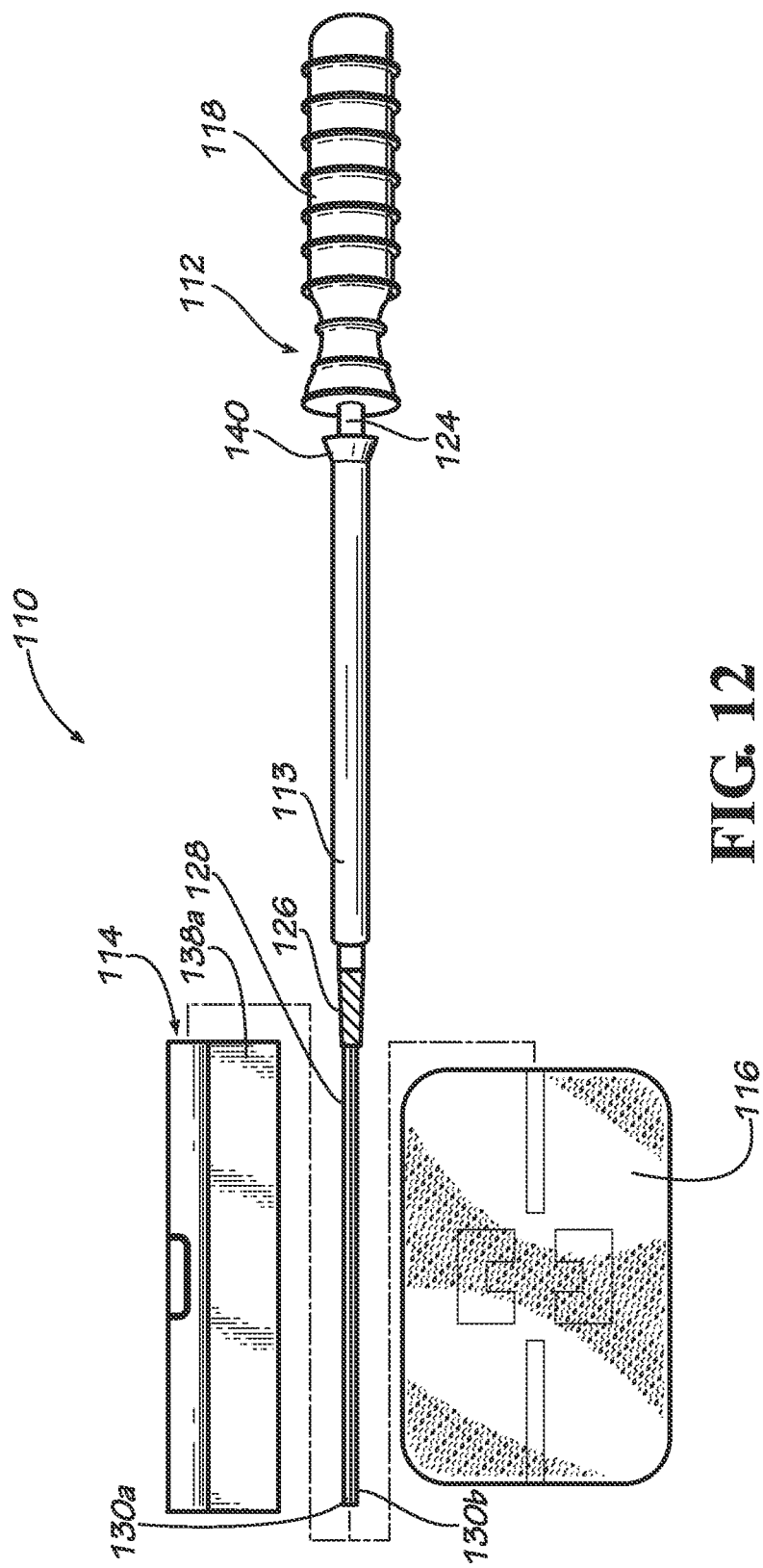
FIG. 12 is a perspective view of an endoscopic system including an introducer, a furler and a mesh according to another embodiment of the instant disclosure.

Referring to FIG. 12 an endoscopic system 110 in accordance with another embodiment of the present disclosure is illustrated. The endoscopic system 110 is similar to the endoscopic system 10. Accordingly, only those components and operative features that are unique to the endoscopic system 110 are described herein.

The endoscopic system 110 includes a sheath 113 that is positionable along a first and second shaft portions 124, 128 of an introducer 112.

Figure 13:
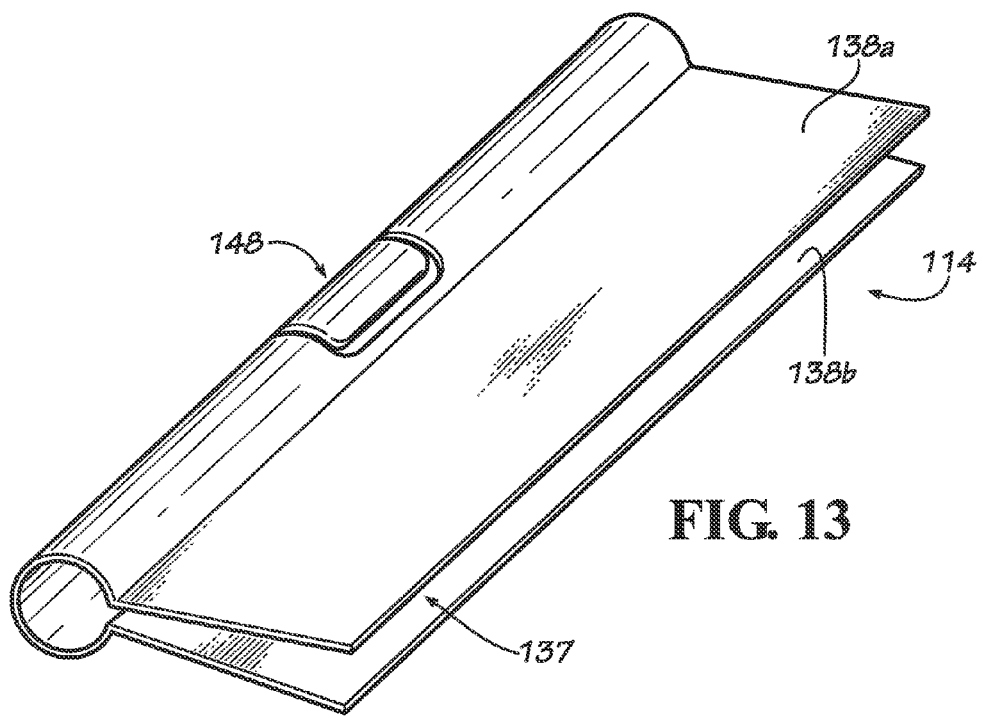
FIG. 13 is a perspective view of the furler shown in FIG. 12.

The endoscopic system 110 includes a furler 114 that is substantially similar to the furler 14 (FIG. 13). Unlike the furler 14, however, the furler 114 illustrated in FIG. 13 is not an "in-line" furler as the furler 14. In other words, the furler 114 is not configured to remain attached to the introducer 112 when a mesh 116 is being inserted through an access port, e.g., the trocar 54. Accordingly, the furler 114 need not include the flared neck portion 40, as this feature (e.g., a flared neck portion 140) is provided on the sheath 113 (see FIG. 12).

Figure 14:
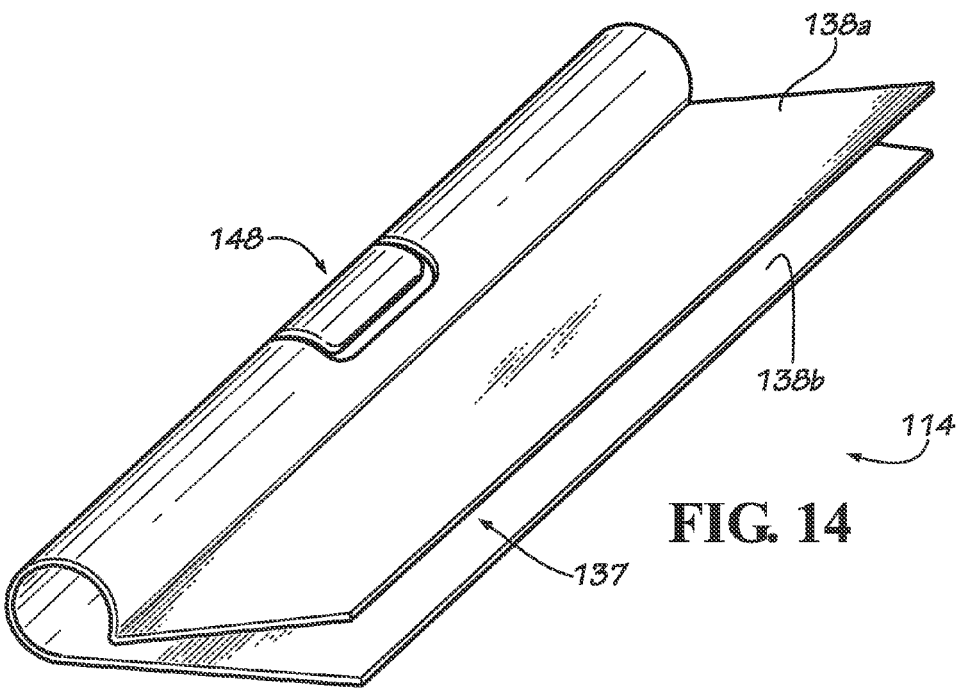
FIG. 14 is a perspective view of a furler according to another embodiment of the instant disclosure.

As illustrated in FIG. 13, the furler 114 includes a longitudinal slot 137 that is defined by a pair of spaced-apart fins or tension tabs 138a, 138b. The tension tabs 138a, 138b define the longitudinal slot 137 along a center of the furler 114 which provides a center "lead-in" for the folded mesh 116 into the furler 114 (FIG. 13). Alternatively, at least one of the tension tabs 138a, 138b extends along a tangent of the furler 114 which provides a tangent "lead-in" for the folded mesh 16 into the furler 114 (FIG. 14).

The longitudinal slot 137 is defined by the tension tabs 138a, 138b and is wider than the longitudinal slot 37 on the furler 14. This wideness of the longitudinal slot 137 facilitates inserting the folded mesh 116 into the furler 114, as the mesh 116 is led into the furler 114 from the center of the furler 114 or the tangent along the furler 14 as opposed to the distal end 38 of the furler 14 described above. Moreover, when the tension tabs 138a, 138b are moved towards one another, the tension tabs 138a, 138b provide an additional force to the mesh 116, thereby facilitating an even tighter wind of the mesh 116.

Referring to FIGS. 15-18, a method of use of the endoscopic system 110 is now described. The components of the endoscopic system 110 may be packaged and shipped separately, or together as a kit. In the latter instance, for example, the kit may include one or more of the aforementioned radial sleeves or trocar 54, the introducer 112, the furler 114, the sheath 113 and the mesh 116.

Figure 15:
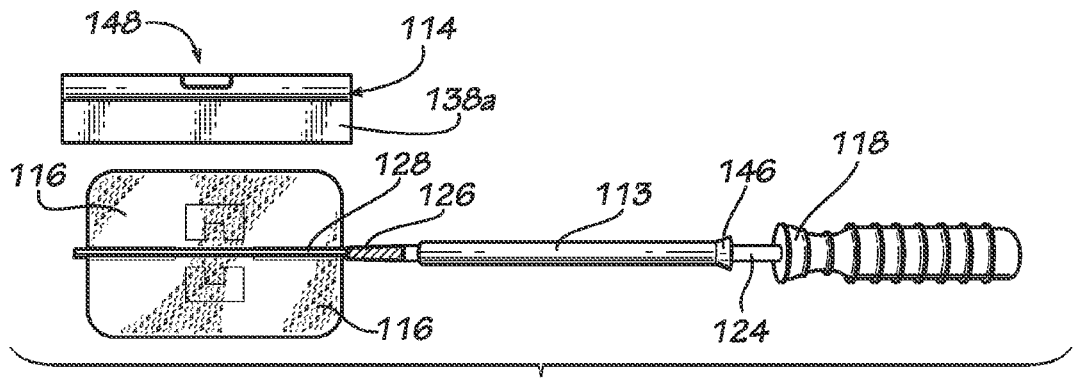
FIGS. 15-18 are perspective views illustrating a method of use of the endoscopic system shown in FIG. 12.
Figure 16:
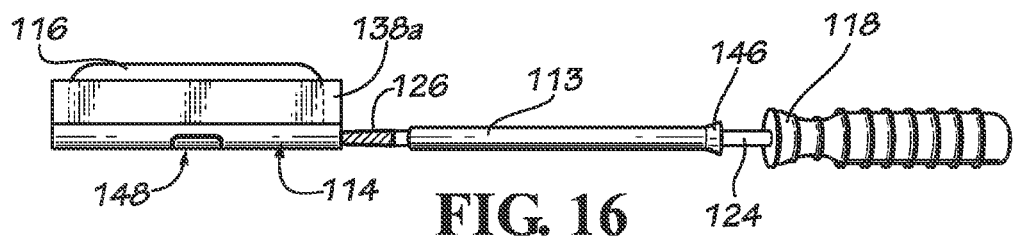

The sheath 113 is, initially, positioned on the first shaft portion 124 adjacent a handle 118, with the tines 130a, 130b exposed or extending distally of the sheath 113 (see FIG. 12 for example). The mesh 116 may be placed flat between the tines 130a, 130b, with the tines 130a, 130b in the center of the mesh 116 (FIG. 15). The mesh 116 is then folded in half along the tines 130a, 130b and the mesh 116 is then inserted into the longitudinal slot 137 of the furler 114 (FIG. 16), which can include either of the configurations of the tensions tabs 138a, 138b shown in FIGS. 13 and 14.

Figure 17:
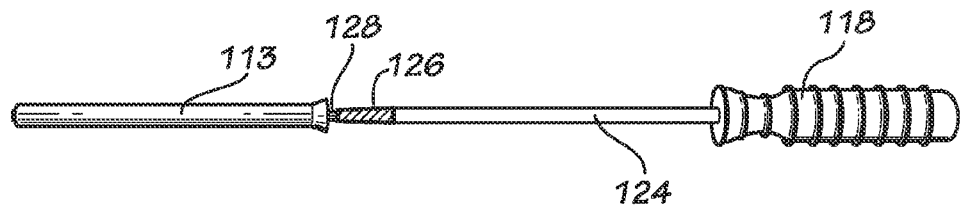

In one hand a surgeon holds the furler 114, and with the other hand rotates the handle 118 of the introducer 112, thereby rolling or winding the mesh 116 within the furler 114. The tabbed cut-out 148 can be depressed (as described above) as the mesh 16 is being wound in the furler 114 to provide a tight wind of the mesh 16. Alternatively, or in addition thereto, the tension tabs 138a, 138b can be moved towards one another, which can also facilitate in providing a tight wind of the mesh 116. Once the mesh 116 is fully wound, the sheath 113 is moved along the first and second shaft portions 124, 128 so that the sheath 113 is positioned within the furler 114 and over the tines 130a, 130b including the wound mesh 116 (FIG. 17). For clarity, the sheath 113 is not explicitly shown positioned within the furler 114. The introducer 112 including the sheath 113 with the wound mesh 116 is then inserted into the trocar 54.

Figure 18:
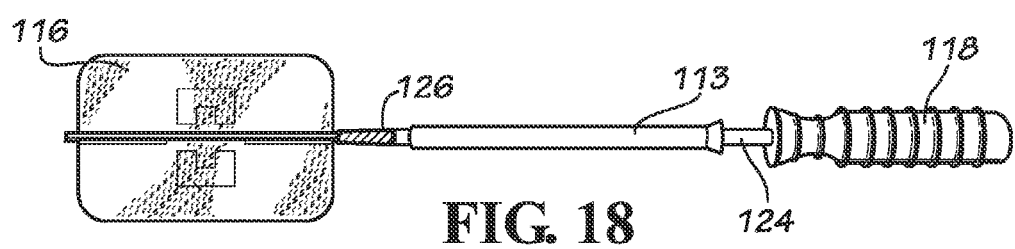

As the introducer 112 is being inserted into the trocar 54, the flared neck portion 140 of the sheath 113 prevents the sheath 113 from going past the trocar 54. As the surgeon continues to insert the introducer 112 via the handle 118, the tines 130a, 130b advance the mesh 116 past the sheath 113/trocar 54 and into the abdominal cavity of the patient, where the mesh 116 naturally unwinds (FIG. 18). At this point the surgeon can use the introducer 112 to roughly position (e.g., via an articulating portion 126 of the introducer 112) the mesh 116 for initial tacking, or simply remove the introducer 112, thereby allowing the mesh 116 to gently drop into the abdominal cavity.

As can be appreciated, the same advantages described above with respect to the endoscopic system 10 are attainable with the endoscopic system 110.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic system for winding and inserting a mesh into an abdominal cavity of a patient, comprising:
    an introducer having an elongated shaft extending distally therefrom, the shaft including a split portion defining an opening therealong, the split portion configured to support the mesh within the opening;
    a furler defining a lumen and being engageable with the split portion of the shaft and configured to exert a radial force onto the mesh that is supported by the split portion, wherein the furler includes a medial portion having a tabbed cut-out defined by three side walls and a living hinge;
    wherein rotation of one of the furler or introducer with respect to the other winds the mesh inside the furler to a diameter smaller than a diameter of the lumen of the furler; and
    wherein the tabbed cut-out is depressible to reduce the diameter of the lumen of the furler and apply a normal force to the mesh as the mesh is being wound within the furler.

2. The endoscopic system according to claim 1, wherein the furler is movable along the shaft to at least partially cover the mesh when the mesh is positioned within the split portion of the shaft.

3. The endoscopic system according to claim 1, wherein the furler has an elongated configuration and a longitudinal slit extending along a length thereof.

4. The endoscopic system according to claim 3, wherein the longitudinal slit of the furler is configured to receive the mesh when the mesh is supported on the split portion of the shaft.

5. The endoscopic system according to claim 1, wherein the furler includes a tapered-down distal end defined by a v-shaped opening.

6. The endoscopic system according to claim 1, wherein the furler includes a flared proximal end having a conical configuration.

7. The endoscopic system according to claim 1, wherein the furler includes a pair of tension tabs extending radially from a center of the furler.

8. The endoscopic system according to claim 1, wherein the furler includes a pair of tension tabs extending tangentially from a center of the furler.

9. The endoscopic system according to claim 1, wherein the shaft includes an articulating portion positioned proximally in relation to the split portion.

10. The endoscopic system according to claim 1, wherein the opening of the split portion extends to a distal tip of the shaft.

11. The endoscopic system according to claim 1, further including a sheath which is movable along the shaft and slidable within the furler.

* * * * *